US012281068B2

(12) United States Patent
Guerret et al.

(10) Patent No.: US 12,281,068 B2
(45) Date of Patent: Apr. 22, 2025

(54) STABLE FORMULATIONS OF 1-Z-BROMOALK-1-ENE COMPOUNDS AND USE THEREOF IN THE MANUFACTURE OF PHEROMONES

(71) Applicant: MELCHIOR MATERIAL AND LIFE SCIENCE FRANCE, Lacq (FR)

(72) Inventors: Olivier Guerret, Pern (FR); Eric Gayon, Monein (FR); Loic Guillonneau, Orleans (FR)

(73) Assignee: MELCHIOR MATERIAL AND LIFE SCIENCE FRANCE, Lacq (FR)

( * ) Notice: Subject to any disclaimer, the term of this patent is extended or adjusted under 35 U.S.C. 154(b) by 747 days.

(21) Appl. No.: 17/623,723

(22) PCT Filed: Jul. 9, 2020

(86) PCT No.: PCT/EP2020/069399
§ 371 (c)(1),
(2) Date: Dec. 29, 2021

(87) PCT Pub. No.: WO2021/009002
PCT Pub. Date: Jan. 21, 2021

(65) Prior Publication Data
US 2022/0259134 A1 Aug. 18, 2022

(30) Foreign Application Priority Data
Jul. 12, 2019 (FR) ........................................ 1907866

(51) Int. Cl.
*C07C 67/08* (2006.01)
*C07C 21/14* (2006.01)
*C07C 29/32* (2006.01)
*C07C 67/62* (2006.01)

(52) U.S. Cl.
CPC .............. *C07C 67/08* (2013.01); *C07C 21/14* (2013.01); *C07C 29/32* (2013.01); *C07C 67/62* (2013.01)

(58) Field of Classification Search
None
See application file for complete search history.

(56) References Cited

U.S. PATENT DOCUMENTS

| 2,355,319 | A |  | 8/1944 | Morris et al. | |
|---|---|---|---|---|---|
| 2,364,588 | A |  | 12/1944 | Morris et al. | |
| 2,376,075 | A |  | 5/1945 | Morris et al. | |
| 3,839,087 | A | * | 10/1974 | Beckers ............... | C23G 5/0289 |
|  |  |  |  |  | 252/396 |
| 4,287,003 | A | * | 9/1981 | Allen ...................... | C07C 17/42 |
|  |  |  |  |  | 134/40 |
| 4,385,192 | A | * | 5/1983 | Friedman .............. | C07C 17/395 |
|  |  |  |  |  | 570/252 |
| 5,395,993 | A |  | 3/1995 | Klein et al. | |
| 6,838,576 | B1 |  | 1/2005 | Wicki et al. | |

FOREIGN PATENT DOCUMENTS

| EP | 0 241 335 A1 | 10/1987 |
|---|---|---|
| EP | 0 630 877 A1 | 12/1994 |

OTHER PUBLICATIONS

Allmendinger et al., "Total Synthesis of Sperabillin A and C." Synlett, No. 17, 2005, pp. 2615-2618.
Cahiez et al., "Gram-Scale, Cheap, and Eco-Friendly Iron-Catalyzed Cross-Coupling between Alkyl Grignard Reagents and Alkenyl or Aryl Halides," Organic Letters, vol. 21, Apr. 9, 2019, pp. 2679-2683.
Cahiez et al., "Highly Stereo- and Chemoselective Iron-Catalyzed Alkenylation of Organomagnesium Compounds," Synthesis, Aug. 1998, pp. 1199-1205.
Cahiez et al., "Iron Thiolate Complexes: Efficient Catalysts for Coupling Alkenyl Halides with Alkyl Grignard Reagents," Chemistry A European Journal, No. 18, 2012, pp. 5860-5863.
Fusini et al., "Identification and synthesis of new sex-specific components of olive fruit fly (*Bactrocera oleae*) female rectal gland, through original Negishi reactions on supported catalysts," Tetrahedron, vol. 74, 2018 (Available online Jul. 6, 2018), pp. 4381-4389.
Mori et al., "Pheromone Synthesis; CXXXIII. Synthesis of Both the Enantiomers of (3Z, 9Z)-cis-6, 7-Epoxy-3,9-nonadecadiene, a Pheromone Component of Erannis defoliaria," Synthesis, Dec. 1991, pp. 1125-1129.
Murahashi et al., "Stereoselective Synthesis of Alkenes and Alkenyl Sulfides from Alkenyl Halides Using Palladium and Ruthenium Catalyts," Journal of Organic Chemistry, vol. 44, No. 14, 1979, XP-002257406, pp. 2408-2417.
Quero et al., "Behavior of Processionary Males (*Thaumetopoea pityocampa*) Induced by Sex Pheromone and Analogs in a Wind Tunnel." Journal of Chemical Ecology, vol. 21, No. 12, 1995 (Accepted Jul. 23, 1995), pp. 1957-1969.

\* cited by examiner

*Primary Examiner* — Amy C Bonaparte
(74) *Attorney, Agent, or Firm* — Birch, Stewart, Kolasch & Birch, LLP

(57) ABSTRACT

The present invention concerns new stable compositions of 1-Z-bromoalk-1-ene compounds of general formula (A). These compositions are characterized in that they also comprise either at least one cyclic ether compound comprising between 4 and 6 carbon atoms, or at least one ether of general formula (B) in which $R_1$ and $R_2$ are identical or different and selected from the group consisting of: a linear or branched alkyl group containing 1 to 8 carbon atoms.

17 Claims, No Drawings

STABLE FORMULATIONS OF 1-Z-BROMOALK-1-ENE COMPOUNDS AND USE THEREOF IN THE MANUFACTURE OF PHEROMONES

FIELD OF THE INVENTION

The present invention relates to novel stable compositions of 1-Z-bromo-alk-1-enes of general formula A:

[Chem.1]

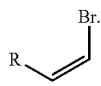

A

These compositions are characterized in that they additionally comprise either at least one cyclic ether compound comprising between 4 and 6 carbon atoms, or at least one ether of general formula B:

[Chem.2]

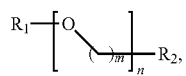

B where $R_1$ and $R_2$ are carbon radicals which do not have a function which is reactive with respect to organomagnesiums or organolithiums.

CONTEXT OF THE INVENTION

Z-Bromovinyl compounds are key intermediates for the manufacture of certain organic molecules and in particular for the manufacture of lepidopteran sex pheromones. Lepidopteran sex pheromones are linear unsaturated organic molecules with 8 to 20 carbon atoms, bearing from 1 to 3 double bonds, optionally conjugated. Further, these molecules are also terminated by an alcohol, aldehyde or acetate type polar function.

The distinctive feature of each sex pheromone lies in the fact that the pheromonal signal emitted by an insect must be specific to that insect alone. This specificity is made possible by the following set of chemical characteristics for a given pheromone molecule:
  linear chain length; normally these chains have an even number of carbon atoms;
  terminal function selected from alcohol, aldehyde and acetate functions;
  number and position of double bonds, as some lepidopteran pheromones differ from each other only by the replacement of a double bond by a triple bond; and
  stereochemistry of each double bond.

Furthermore, for a given pheromonal signal, several of these molecules can be combined into a pheromonal bouquet in variable proportions, which multiplies the possibilities of pheromonal signal specificity.

For example, considering the family of 11-hexadecenol derivatives, it is observed that:
  -Z-11-hexadecenol and its acetate are the two components of the pheromone bouquet of the Mediterranean Corn Borer causing havoc in both Europe and Africa, while its E-isomer does not contribute significantly.
  -Z-11-hexadecenal is, on the one hand, the major component (80%) of the pheromones of the box tree moth (in combination with its E-isomer); it is also the main component (95%) of the pheromones of the Cotton Bollworm but also of the rice borer (Chilo suppressalis) whereas E-hexadecenal does not contribute to their pheromonal bouquets as cited on the web site www.pherobase.com.

Another example is the pheromone bouquet of the oak processionary, which consists mainly of (Z,Z)-11,13-hexadecadienyl acetate, the (E,Z) isomer of which is an insect repellent.

This shows how important the selectivity of the chemical structures that the person skilled in the art has to prepare is when it comes to preparing an insect-specific pheromone(s) (see for example Quero et al. J. Chem. Ecology Food. Chem. 1995, 21, 1957-1969). Now, the skilled person needs to reproduce these pheromones synthetically so as to be able to use them in the context of biological control of crop pests.

In the context of the preparation of lepidopteran sex pheromones, which are, it should be recalled, linear organic molecules of 8 to 20 carbon atoms, carrying from 1 to 3 double bonds, optionally conjugated, the skilled person has at his or her disposal various methods for creating double bonds in long aliphatic chains described in the prior art.

The methods of choice for creating double bonds in long aliphatic chains are primarily the Wittig or Wittig-Horner reactions. A number of examples of the use of such reactions exist in the literature (see for example patents EP0630877, US 5395993, US 6838576, EP0241335B1). These reactions between an aldehyde and a phosphorus ylide lead to Z/E selectivities comprised between $^{80}/_{20}$ and $^{92}/_{8}$. Another method of choice consists in coupling of halogenated vinyls with a Grignard reagent or an alkynide in the presence of a metal catalyst (see for example Cahiez, G.; Avedissian, H. Synthesis 1998, 1199; Cahiez, G. et al. Chem. Eur. J. 2012, 18, 5860). This method is much more stereoselective since it retains the configuration of the starting halogenated compound: if the skilled person has a halogenated vinyl compound exclusively in the Z configuration, the olefin obtained after coupling will have an equivalent configuration (Quero et al. J. Chem. Ecology Food. Chem. 1995, 21, 1957-196). The best yields are obtained when the vinyl compound is a brominated compound.

This last method has the advantage of not generating phosphorus effluents. However, the difficulty of the industrial transposition of this last method lies mainly in the access to brominated vinyl compound products whose cis/trans isomer ratio would be sufficiently stable so that they can be preserved under economic conditions until their use as intermediates for the synthesis of organic molecules such as these pheromones, especially since their use can be done on an industrial site different from the one where they were produced.

Furthermore, the synthesis of certain organic molecules such as lepidopteran sex pheromones requires the use of organomagnesium or organolithium which are known to react by nucleophilic addition with epoxides, ketones and unsaturated 1-4 ketones and by acid-base reaction with alcohols.

There is therefore a real need for brominated vinyl compounds whose cis/trans isomer ratio is sufficiently stable to be retained until the use of said compounds as synthetic intermediates and whose storage medium is compatible with a subsequent reaction with an organomagnesium or organolithium.

PRIOR ART

Techniques for stabilizing halogenated vinyl compounds have been studied in the past; we can cite for example patents US2364588, US2355319 and US2376075. However, these three patents only relate to the stabilization in the broad sense of halogenated butenes, without specifying the stereochemistry of the compound to be stabilized nor the stereochemistry of the compound persisting or obtained after a storage time. These three patents therefore do not allow the person skilled in the art to find a solution for stabilizing the stereochemistry of 1-Z-bromoalkene compounds. Moreover, they do not deal with the problem of having a storage medium that is compatible with a subsequent reaction with an organomagnesium or organolithium.

SUMMARY OF THE INVENTION

In the context of the present invention, the inventors have surprisingly discovered that, in a composition comprising 1-Z-bromoalkene compounds, the presence of 0.5% to 30% by weight of an ether which is non-reactive with respect to organomagnesiums or organolithiums, based on the total weight of the composition, preserves the stereochemistry of said 1-Z-bromoalkene compound over time and thus to render 1-Z-bromoalkene compounds industrially exploitable.

Another interest of these compositions is that they are compatible with their subsequent use of coupling with an organomagnesium compound; the organomagnesium compounds are generally also stabilized by ethers. Another object of the invention is therefore the use of these compositions for the manufacture of pheromones carrying double bonds via organometallic couplings in the presence of organomagnesiums or organolithiums.

According to a first aspect, the present invention thus relates to a composition comprising:

a 1-Z-bromo-alk-1-ene of general formula A:

[Chem.3]

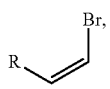

A where R is a linear alkyl group having between 1 and 24 carbon atoms; and
either at least one cyclic ether whose ring comprises between 4 and 6 carbon atoms, optionally substituted by a C1-C3 alkyl group, preferably by a methyl;
or at least one ether of general formula B:

[Chem.4]

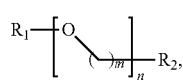

B where n is comprised between 1 and 4 and m is comprised between 0 and 5, particularly between 1 and 5, preferably m is comprised between 1 and 3; and R1 and R2, identical or different, are selected from the group comprising: a linear or branched alkyl group having 1 to 8 carbon atoms.

According to a second aspect, the present invention relates to the use of a composition according to the invention in a coupling reaction of the compound 1-Z-bromoalk-1-ene of general formula A with a compound selected from the group comprising organomagnesiums and organolithiums.

According to a third aspect, the present invention relates to the use of a composition according to the invention for the manufacture of fatty chain pheromone.

DETAILED DESCRIPTION OF THE INVENTION

In the sense of the present invention, "storage medium which is compatible with subsequent reaction with an organomagnesium or organolithium" means a storage medium in which only the 1-Z-bromoalk-1-ene compound(s) of general formula A is (are) capable of reacting with organomagnesiums or organolithiums.

In the sense of the present invention, "organomagnesium" means an organic compound having a carbon-magnesium bond. The family of organomagnesium compounds includes, but is not limited to, the Grignard reagents, which are mixed organomagnesium compounds of formula R'-MgX, where R' is a carbon chain and X is a halogen, and in particular the compounds of general formula $Y—(CH_2)_n—MgX$, where n is an integer comprised between 2 and 20, preferably n is comprised between 6 and 12, and where Y is an ether, alcoholate (—OMgX), acetylate (—OC(O)CH3) or acetal function (

[Chem.5]

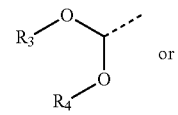

or

[Chem.6]

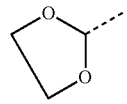

with R3 and R4 being C1-8 alkyl chains, identical or different, preferably R3 and R4 are selected from methyl, ethyl or propyl groups).

In the sense of the present invention, "organolithium" means an organometallic compound having a carbon-lithium bond. Organolithium compounds include, but are not limited to, lithium alkyls such as methyllithium, butyllithium or hexyllithium or compounds of general formula R"-Li, where R" is a carbon chain, and in particular the compounds of general formula $Y\text{-}(CH_2)_n\text{-}Li$ where n is an integer comprised between 2 and 20, preferably n is comprised between 6 and 12, and where Y is an ether, alcoholate (—OLi), acetylate (—OCCH3) or acetal function

[Chem.7]

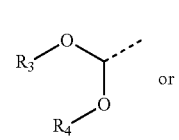

or

[Chem.8]

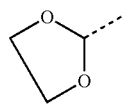

with R3, R4 C1-C8 alkyl chains, identical or different, preferably selected from methyl, ethyl or propyl groups).

In the sense of the present invention, "labile hydrogen" means a hydrogen atom having an acidic character such as, for example, but not limited to, the hydrogen of alcohols, carboxylic acids, amines, and primary and secondary amides. Thus, an ether that does not include labile hydrogen is unlikely to generate protons.

A first object of the present invention is a composition comprising:

a 1-Z-bromo-alk-1-ene of general formula A:

[Chem.9]

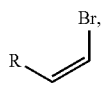

where R is a linear alkyl group having between 1 and 24 carbon atoms; and
either at least one cyclic ether whose ring comprises between 4 and 6 carbon atoms, optionally substituted by a C1-C3 alkyl group, preferably by a methyl; or at least one ether of general formula B:

[Chem.10]

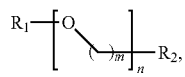

where n is comprised between 1 and 4 and m is comprised between 0 and 5, in particular between 1 and 5, preferably m is comprised between 1 and 3; and R1 and R2, identical or different, are selected from the group comprising: a linear or branched alkyl group having 1 to 8 carbon atoms.

According to a preferred embodiment, the cyclic ether is selected from tetrahydrofuran, methyl tetrahydrofuran and dioxane.

According to an embodiment, the group R of the compound of general formula A is selected from the group comprising methyl, ethyl, propyl, butyl, pentyl, hexyl, heptyl, octyl, nonyl, decanyl, undecanyl, dodecanyl, tridecanyl, tetradecanyl, pentadecanyl, hexadecanyl, heptadecanyl and octadecanyl groups.

According to an embodiment, the groups R1 and R2 of the compound of general formula B, identical or different, are selected from the group comprising methyl, ethyl, isopropyl, tert-butyl and neopentyl groups. Advantageously, the compound B is methyl tert-butyl ether. According to an embodiment, the 1-Z-bromoalk-1-ene content in the composition according to the invention is comprised between 70 and 99.5% by weight, preferably between 90 and 99% by weight and still more preferentially between 93 and 98% by weight, based on the total weight of said composition.

According to an embodiment, the ether content in the composition according to the invention is comprised between 0.5 and 30% by weight, preferably between 1 and 10% by weight and still more preferentially between 3 and 10% by weight, based on the total weight of said composition.

A second object of the present invention is the use of the composition according to the invention in a coupling reaction of a compound of general formula A with a compound selected from the group comprising organomagnesiums and organolithiums.

According to an embodiment, the invention relates to the use of the composition according to the invention in a coupling reaction of a compound of general formula A with an organomagnesium compound of formula R'-MgX, wherein R' is a carbon chain and X is a halogen. According to a preferred embodiment, said organomagnesium compound has the general formula Y-$(CH_2)_n$-MgX where n is an integer comprised between 2 and 20, preferably n is comprised between 6 and 12, and where X is a chlorine or bromine atom and where Y is an ether, alcoolate (—OMgX), acetylate (—OC(O)CH3) or acetal function (

[Chem.11]

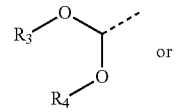 or

[Chem.12]

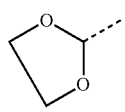

with R3 and R4 being C1-C8 alkyl chains, identical or different, preferably R3 and R4 are selected from methyl, ethyl and propyl groups). Preferably, the reaction takes place in the presence of a catalyst. According to another embodiment, the invention relates to the use of the composition according to the invention in a coupling reaction of a compound of general formula A with an organolithium compound of general formula Y-$(CH_2)_n$-Li where n is an integer comprised between 2 and 20, preferably n is comprised between 6 and 12, and where Y is an ether, alcoholate (—OLi), acetylate (—OC(O)$CH_3$) or acetal function (

[Chem.13]

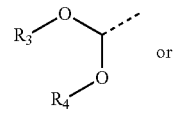 or

[Chem.14]

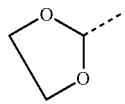

with R3 and R4 being C1-C8 alkyl chains, identical or different, preferably R3 and R4 are selected from methyl, ethyl and propyl groups). Preferably, the reaction takes place in the presence of a catalyst. A third object of the present invention is the use of a composition according to the invention for the manufacture of fatty chain pheromone.

According to an embodiment, the invention relates to the use of the composition according to the invention for the manufacture of lepidopteran pheromone carrying at least one unsaturation in a Z-configuration via a coupling reaction in the presence of an organomagnesium or an organolithium and a metal complex. According to an embodiment, the compositions according to the invention are used for the synthesis of compounds selected from: Z-7-decen-1-yl acetate, Z-9-dodecen-1-yl acetate, Z-9-dodecen-1-ol, Z-11-tetradecen-1-ol, Z-11-tetradecen-1-ol, Z-11-tetradecen-1-yl acetate, Z-11-tetra-decenal, (Z)-hexadec-13-en-11-yn-1-yl acetate, (Z,Z)-11,13-hexadecadien-1-yl-acetate and (Z,Z)-11,13-hexadecadienal. According to an embodiment, the compositions according to the invention are used for the synthesis of compounds selected from: Z-5-decen-1-ol, Z-5-decen-1-yl acetate, Z-7-dodecen-1-ol, Z-7-dodecen-1-yl acetate, Z-9-tetradecen-1-ol, Z-9-tetradecen-1-yl acetate, Z-9-tetradecenal, Z-11-hexadecen-1-ol, Z-11-hexadecen-1-yl acetate, Z-11-hexadecenal, Z-13-octadecen-1-yl acetate and Z-13-octadecenal. The following examples are intended to illustrate the present invention in a non-limiting manner and will provide a better understanding of the invention and its scope.

EXAMPLES

The synthesis of the precursor α,β-di-bromo acids of the compounds according to the invention are obtained according to the procedure described in the publication K. Mori, J.-L. Brevet, Synthesis, 1991, 1125.

The analytical method consists of gas chromatography (GC) analysis on an HP 5890 Series II instrument. The chromatographic column is an Optima delta 6.30 μm, 0.25 mm, 0.25 μm column.

The oven follows the following temperature profile: Initial temperature: 40° C., Initial time 5 min; Gradient 5°/min, Final temperature: 125° C., Duration 15 min. The injector temperature is 250° C., the detector temperature is 280° C., the injected volume is 1 μL and the pressure is 6 psi. The sample concentration is 75 g/L in tetrahydrofuran (THF).

The reactions are carried out in a 20 L jacketed glass reactor and the distillations are carried out using a glass column with 10 theoretical trays.

Example 1: Preparation of 1-Z-bromobut-1-ene

In a clean reactor previously purged with nitrogen, the following are successively introduced:
2,3-dibromopentanoic acid: 3.830 kg with a mass purity of 86.6% (1 eq); and
dimethylformamide (DMF): 7.660 L (2 vol).

The coolant is cooled to −15° C. The solution is then heated to 55° C., then an aqueous solution of 50 wt. % of soda is added at a rate that controls the $CO_2$ produced by the decarboxylation reaction and maintains the temperature of the reaction medium between 53° and 80° C.

At the end of the addition of the aqueous solution with 50 wt. % of soda, the temperature of the reactor is increased to 110° C., first under atmospheric pressure, then under reduced pressure at 100 mbar so as to remove the water and the last traces of product.

The good distillation fractions are then collected and the organic solvent (DMF) is removed by water wash.

1-Z-Bromobut-1-ene (1.414 kg) with an isomer excess of 99.8/0.2 and a mass purity >99% is obtained. The water content measured by Karl Fischer titration is less than 0.15%.

Example 2: Preparation of 1-Z-bromohex-1-ene

In a clean reactor previously purged with nitrogen, the following are successively introduced:
2,3-dibromoheptanoic acid: 3.5 kg with a mass purity of 88% (1 eq); and
dimethylformamide (DMF): 6.3 L (2 vol)

The coolant is cooled to −15° C.

The solution is then heated to 55° C., then an aqueous solution of 50 wt. % of soda is added at a rate that allows the $CO_2$ produced by the decarboxylation reaction to be controlled and the temperature of the reaction medium to be maintained between 53° and 80° C.

At the end of the addition of the aqueous solution with 50 wt. % of soda, the temperature of the reactor is increased to 110° C., first under atmospheric pressure, then under reduced pressure at 100 mbar so as to remove the water and the last traces of product.

The good distillation fractions are then collected and the organic solvent (DMF) is removed by water wash.

1-Z-Bromohex-1-ene (1.175 kg) is obtained with an isomer excess of 99.7/0.3 and a mass purity >99%.

Example 3: Preparation of Compositions According to the Invention

A proportion (in %) of an ether is added to the 1-Z-bromobut-1-ene of Example 1 (denoted C4) or to the 1-Z-bromohex-1-ene of Example 2 (denoted C6), and the stability of the Z/E ratio is studied by considering the number of days from which the Z/E ratio reaches a level of less than 95% of the Z isomer under temperature-controlled aging conditions (denoted T95). The data on the studied compositions are collected in the following table:

TABLE 1

|  | Formulation no. | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Bromoalkene | C4 | | | | | C6 | | | | |
| Ether added | none | THF | MTBE | MTBE | MTBE | None | THF | MTBE | MTBE | MTBE |
| Weight % of ether | 0 | 5 | 3 | 4.5 | 9 | 0 | 5 | 3 | 4 | 9 |
| Initial Z/E ratio | 97.1/2.9 | | 99.8/0.2 | | | | | 99.7/0.3 | | |

TABLE 1-continued

| | Formulation no. | | | | | | | | | |
|---|---|---|---|---|---|---|---|---|---|---|
| | 1 | 2 | 3 | 4 | 5 | 6 | 7 | 8 | 9 | 10 |
| Storage temperature (° C.) | 4 | 25 | 25 | 25 | 4 | 4 | 25 | 25 | 25 | 4 |
| T95 (days) | 3 | >85 | >285 | 160 | >203 | 20 | >85 | >85 | >85 | >85 |

MTBE = methyl tert-butyl ether

The inventors have thus demonstrated that the ether-free compositions exhibit an isomer ratio which goes from 97.1/2.9 to 95/5 at 4° C. in 3 days in the case of 1-Z-bromobut-1-ene and from 99.7/0.3 to 95/5 at 4° C. in 20 days in the case of 1-Z-bromohex-1-ene. On the other hand, all the compositions having even a limited proportion of an ether lead to stereochemical stabilities over durations of more than 30 days at 25° C., which makes them suitable for use in a multi-step synthesis process. The THF and MTBE selected for this example are conventional solvents for making or using organomagnesiums or organolithiums.

Example 4: Preparation and stability of compositions outside the invention

Either 5% of an alkene type solvent (amylene), or toluene, or a chlorinated solvent (dichloromethane) is added to the 1-Z-bromobut-1-ene of Example 1. In the case of compositions comprising the alkene (amylene) type solvent or toluene, the T95s are 9 and 10 days respectively. In the case of the composition comprising the chlorinated solvent (dichloromethane), the T95 is higher than 20 days but the introduced dichloromethane reacts violently with the organolithiums and organomagnesiums.

Example 5: Use of Composition 9 of Example 3 in reaction with BrMgO-(CH$_2$)$_{10}$-MgBr for the manufacture of Z-11-hexadecenol A 1 mol/L solution (44 mL) of the organomagnesium BrMgO-(CH$_2$)$_{10}$-MgBr obtained from chlorodecanol is introduced under argon at 25° C. into a dry 250 mL four-necked round-bottom flask equipped with a thermometer and mechanical stirring. Then 45 mL of THF is added. The mixture is cooled to −5° C. One portion (14 mg) of iron(III) acetylacetonate is added. The walls of the four-necked round-bottom flask are rinsed with 4 mL THF. (Z)-Bromohex-1-ene (6.52 g) is then introduced over 5 minutes while maintaining a temperature comprised between −5° C. and 0° C. Stirring is maintained at this temperature for 20 minutes.

A 1 mol/L HCl solution (80 mL) is added while keeping the temperature below 30° C. The two phases obtained are separated: the aqueous phase is extracted with 3×20 mL petroleum ether; the organic phases are combined, dried over MgSO4, filtered and concentrated on a rotary evaporator. The residual oil is distilled under vacuum. Boiling temperature at 0.04 mmHg =118° C. A colorless oil (8.6 g) composed of a mixture of the Z and E isomers of 11-hexadecenol (89% yield) with a Z/E isomer ratio of ⁹⁷⁄₃ is then obtained.

Example 6: Use of Composition 5 of Example 3 for the synthesis of pine processionary pheromone ((Z)-hexadec-13-en-11-yn-1-yl acetate)

Diethylamine (35 mL) is loaded (temperature: 19° C., colorless medium) into a 250 mL triple-necked round-bottom flask equipped with magnetic stirring, at room temperature, and then the reaction medium is inerted by a vacuum/nitrogen sequence.

10 mL of previously inerted diethylamine is taken to solubilize 10 g of 11-dodecynol.

20 mg of PdCl2 (orange medium) and 54 mg of CuCl (blue/violet medium) are then added to the triple-necked round-bottom flask. After the medium is homogenized, a vacuum/nitrogen inerting is carried out (the medium becomes green, small endotherm of 5° C.).

9.7 g of 1-bromobut-1-ene solution having 9% of THF is introduced dropwise into the medium.

The docec-11-yn-1-ol in solution in diethylamine is then added dropwise.

Stirring is maintained at 60° C. for 5 h until the medium turns light brown.

At the end of the reaction, 50 mL of 0.1 N hydrochloric acid solution is added and then several extractions with methyl cyclohexane are performed. After evaporation of this solvent 12.6 g of 97% (Z)-hexadec-13-en-11-yn-1-yl acetate with a Z/E isomer ratio of 98/2 is obtained.

The invention claimed is:

1. A composition comprising:
a 1-Z-bromoalk-1-ene of general formula A:

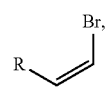

wherein R is a linear alkyl group having from 1 to 24 carbon atoms; and
an ether which is:
either a cyclic ether having a ring comprising from 4 to 6 carbon atoms, optionally substituted by a C1-C3 alkyl group,
or an ether of general formula B:

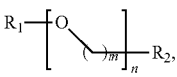

wherein n is from 1 to 4; m is from 0 to 5; and R$_1$ and R$_2$, identical or different, are selected from the group consisting of a linear or branched alkyl group having from 1 to 8 carbon atoms;
wherein the 1-Z-bromoalk-1-ene has a content in the composition from 70 to 99.5% by weight based on the total weight of the composition.

2. The composition according to claim 1, wherein the cyclic ether has a ring comprising from 4 to 6 carbon atoms, optionally substituted by a methyl.

3. The composition according to claim 1, wherein m is from 1 to 3.

4. The composition according to claim 1, wherein the content of 1-Z-bromoalk-1-ene in the composition is from 90 to 99% by weight based on the total weight of the composition.

5. The composition according to claim 1, wherein the content of 1-Z-bromoalk-1-ene in the composition is from 93 to 98% by weight based on the total weight of the composition.

6. The composition according to claim 1, wherein R is selected from the group consisting of methyl, ethyl, propyl, butyl, pentyl, hexyl, heptyl, octyl, nonyl, decanyl, undecanyl, dodecanyl, tridecanyl, tetradecanyl, pentadecanyl, hexadecanyl, heptadecanyl and octadecanyl.

7. The composition according to claim 1, wherein $R_1$ and $R_2$, identical or different, are selected from the group consisting of methyl, ethyl, isopropyl, tert-butyl and neopentyl.

8. The composition according to claim 1, wherein the cyclic ether is selected from the group consisting of tetrahydrofuran, methyl tetrahydrofuran and dioxane.

9. The composition according to claim 1, wherein the ether has a content in the composition from 0.5 to 30% by weight based on the total weight of said composition.

10. The composition according to claim 1, wherein the ether has a content in the composition from 1 to 10% by weight based on the total weight of said composition.

11. The composition according to claim 1, wherein the ether has a content in the composition from 3 to 10% by weight based on the total weight of said composition.

12. A method for coupling a compound of general formula A:

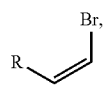

A wherein R is a linear alkyl group having from 1 to 24 carbon atoms,
with a compound selected from the group consisting of organomagnesiums and organolithiums, comprising reacting a composition according to claim 1 with the compound selected from the group consisting of organomagnesiums and organolithiums.

13. The method according to claim 12, wherein the compound selected from the group consisting of organomagnesiums and organolithiums is an organomagnesium compound of general formula Y-$(CH_2)_n$-MgX,
wherein n is an integer from 2 to 20; X is a chlorine or bromine atom; and Y is an ether function; or an alcoholate function selected from the group consisting of —OMgX, —OC(O)CH$_3$,

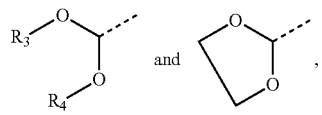

with $R_3$ and $R_4$, identical or different, being a C1-C8 alkyl.

14. The method according to claim 13, wherein $R_3$ and $R_4$, identical or different, are selected from the group consisting of methyl, ethyl and propyl.

15. The method according to claim 12, wherein the compound selected from the group consisting of organomagnesiums and organolithiums is an organolithium compound of general formula Y-$(CH_2)_n$-Li,
wherein n is an integer from 2 to 20, and Y is an alcoholate function selected from the group consisting of —OLi, —OC(O)CH$_3$,

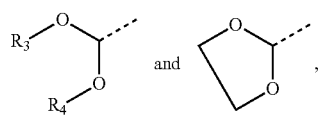

with R3 and R4, identical or different, being a C1-C8 alkyl.

16. The method according to claim 15, wherein $R_3$ and $R_4$, identical or different, are selected from the group consisting of methyl, ethyl and propyl.

17. The method according to claim 12, wherein coupling of the compound of general formula A with the compound selected from the group consisting of organomagnesiums and organolithiums leads to manufacturing a fatty chain pheromone.

* * * * *